United States Patent [19]

Arisland

[11] 3,948,290

[45] Apr. 6, 1976

[54] MEANS FOR CONNECTING AN ELASTOMERIC TUBING TO A MEMBER

[75] Inventor: Kjell Oystein Arisland, St. Catharines, Canada

[73] Assignee: A/S Alto, Oslo, Norway

[22] Filed: June 6, 1974

[21] Appl. No.: 477,086

[30] Foreign Application Priority Data
June 6, 1973 Norway................................ 2370/73

[52] U.S. Cl. ................... 138/89; 138/109; 220/307; 220/356
[51] Int. Cl.² .......................................... F16L 55/10
[58] Field of Search .............. 138/89, 90, 96 R, 109, 138/178; 220/352, 356, 307; 137/377, 380–382; 285/DIG. 2

[56] References Cited
UNITED STATES PATENTS

| | | |
|---|---|---|
| 2,321,667 | 6/1943 | Foster ................................ 220/356 |
| 2,394,875 | 2/1946 | Rommel ............................. 138/89 X |
| 3,410,448 | 11/1968 | Hudson ................................ 220/356 |
| 3,513,849 | 5/1970 | Vaillancourt et al. ......... 285/DIG. 2 |
| 3,633,586 | 1/1972 | Sheridan ....................... 285/DIG. 2 |
| 3,744,528 | 7/1973 | Vestal ................................... 138/89 |

*Primary Examiner*—Richard C. Queisser
*Assistant Examiner*—Charles Gorenstein
*Attorney, Agent, or Firm*—Howson and Howson

[57] ABSTRACT

Closure of the end of an elastomeric tubing is provided by folding the end of the tube back on itself to form a band-like wrap, and inserting into the tube beneath the wrap the solid body of a plug of elastomeric material having at its outer end a resilient tubular portion which is then folded back outside and rearwardly beyond the wrap. Preferably the end of the plug inside the tube is also provided with an axial tubular portion, which extends further into the elastomeric tubing. The construction holds the plug in against gas pressure in the tube, and is suitable for use in the outer end of a catheter tube.

3 Claims, 1 Drawing Figure

U.S. Patent April 6, 1976 3,948,290
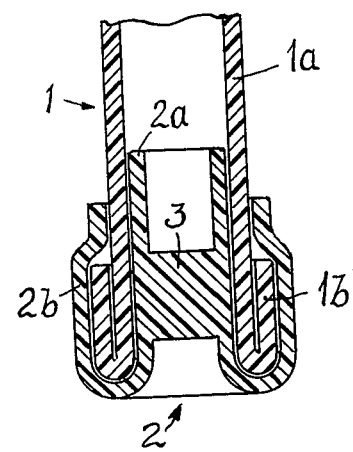

MEANS FOR CONNECTING AN ELASTOMERIC TUBING TO A MEMBER

This invention relates to a means for connecting an elastomeric tubing to a member, said member comprising a relatively solid portion, such as a valve for a surgical or veterinary balloon catheter, and an extension in the form of an elastomeric pipe stub, see f. inst. British Pat. specification No. 1,078,650.

As well known it is difficult to obtain a reliable and safe connection of an elastomeric tubing of rubber latex or a rubber-like material, such as silicon rubber, to different devices. In connection with the valves used in once-for-all balloon or Foley catheters for surgical use, this problem is especially dominant. One has hitherto tried to solve the problem by keeping the valve in place on the catheter by means of a clamp in the form of a short cylinder of rubber. However, such rubber clamps do not solve the problem in a sufficiently satisfactory way, because the forces exerted by the rubber clamp on the tubing and the valve are constant and do not increase at increasing pressure in the tubing and the balloon. Moreover, the clamp represents an extra part of the catheter which, else, only consists of two parts. In connection with mass production every such additional part represents an enhancement in the price.

The object of the invention is to provide a means for connecting an elastomeric tubing to a device in such way that the retaining force will increase with the pressure in the tubing, and which does not require an extra clamping device. According to the invention this is obtained thereby that the end of the elastomeric tubing which is to be connected with the said member, is turned back to form a wrap and that, after said member having been introduced into said end of the tubing, the pipe stub of said member is turned back (wrapped) on the outside of the wrap of the tubing with both said wraps located on the outside of the relatively solid portion of the member.

Thereby is obtained a safe connection or fixing together of the two parts, which is further increased if the free end of the wrap of the member's pipe stub protrudes past the wrap of the tubing. Preferably, the member to be connected is extended by a second pipe stub oppositely directed in relation to the first pipe stub and at least partly located within the wrap of the first pipe stub of said member.

The means according to the invention used for instance in connection with balloon catheters solves the problem to fix a valve device to an elastomeric tubing for instance of silicon rubber or latex in such a way that complete tightening is obtained with certainty. Moreover, the means according to the invention may be used on all the fields of medicine, industry etc. in which it is important to secure a member to an elastomeric tubing.

An embodiment of the invention is shown in axial section in the drawing. A tubing 1 to be connected with a member 2 is of elastomeric material, such as silicon rubber or another elastic material. The end $1a$ of said tubing 1 which is to be connected with said member 2 is turned back so that its end portion is located on the outside of the tubing to form a wrap $1b$. The member 2 to be connected has a relatively solid portion 3 which may for instance comprise a valve not shown. Portion 3 may also be made of solid rubber which, when a balloon of a balloon catheter connected with the other end of the tubing 1 is to be filled with air, is pierced through by a hypodermic needle for pumping of air into the balloon. The relatively solid portion 3 has a pipe stub $2b$ which is also turned back to form a wrap on the outside of the wrap $1b$ on the end $1a$ of tubing 1. This pipe stub $2b$ forms the outer part of the valve device, from the other or inner end of which there protrudes a second pipe stub $2a$. The free end of the wrap $2b$ preferably extends past wrap $1b$, and both wraps are located on the outside of the relatively solid portion 3. The second pipe stub $2a$ serves as a centering and supporting means for the tubing 1 and member 2 with the extension with wrap $2b$.

A pressure in the tubing $1a$ which tries to push the valve device out of the tubing, will increase the friction between the parts and thereby result in a better fit. Should the construction loosen after all due to a large inner pressure in the tubing 1, the wrap $1b$ must first be forced back.

I claim:

1. A closure assembly for a resilient elastomeric tube, comprising:
    an integral turned-back elastic outer wrap formed from, and at, the end of said elstomeric tube;
    a plug member of elastomeric material having a relatively solid body portion positioned within said wrap and of a size to form a tight fit between said body and the interior of said wrap;
    said plug member having an integral resilient tubular portion extending outward from said end of said tube and folded back to a position overlying said wrap and said body portion, whereby both said wrap and said folded back portion of said member exert a radially-inward elastic pressure on said body portion of said member.

2. The assembly of claim 1, in which said folded-back portion of said plug member extends rearward beyond said turnedback wrap of said tube, further to enhance the resistance of said plug member to expulsion by gas pressure in said tube.

3. The assembly of claim 2, in which said plug member comprises another integral tubular portion extending into said tube from said body portion and forming a close fit with the interior of said tube.

* * * * *